Figure 1:
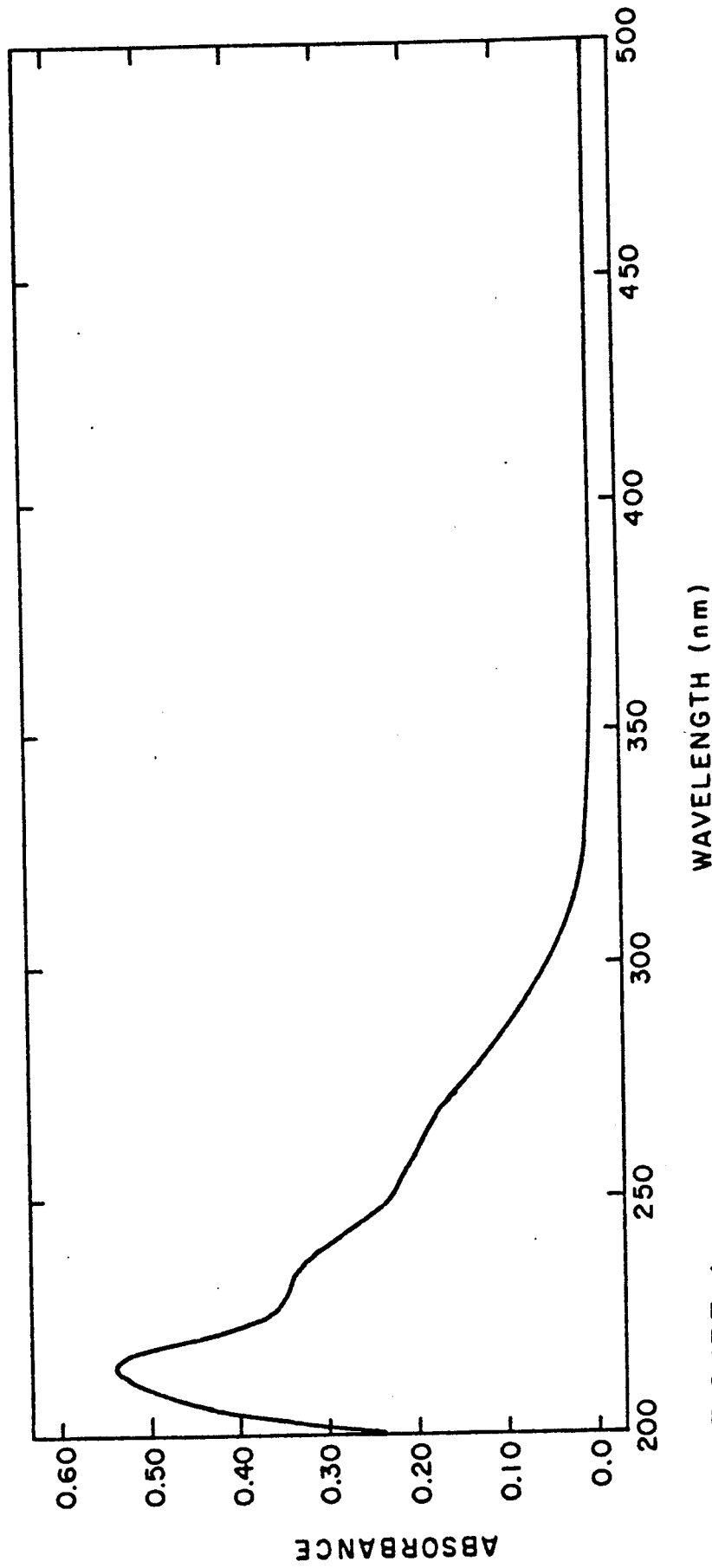
Figure 2:
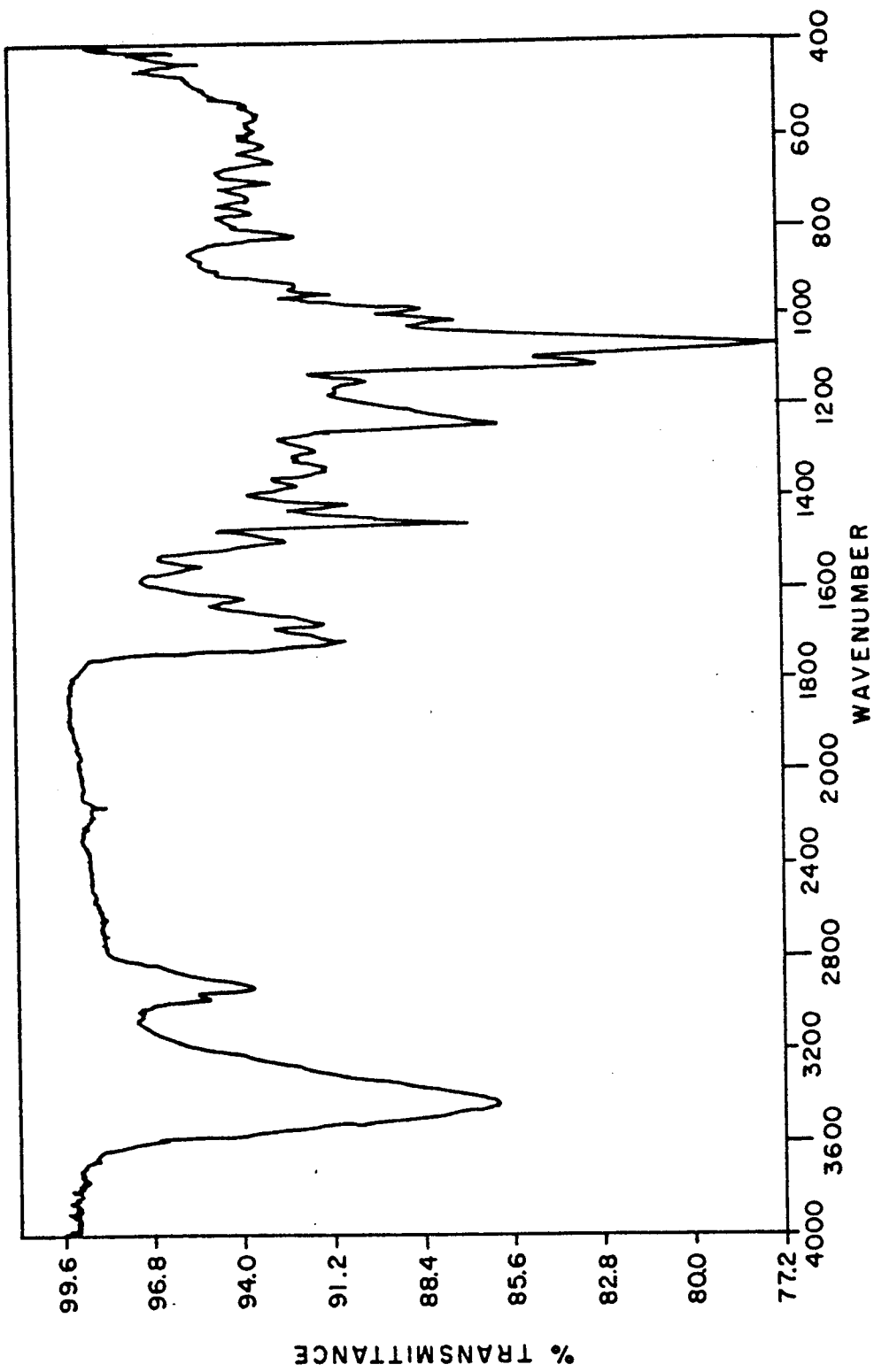
Figure 3:
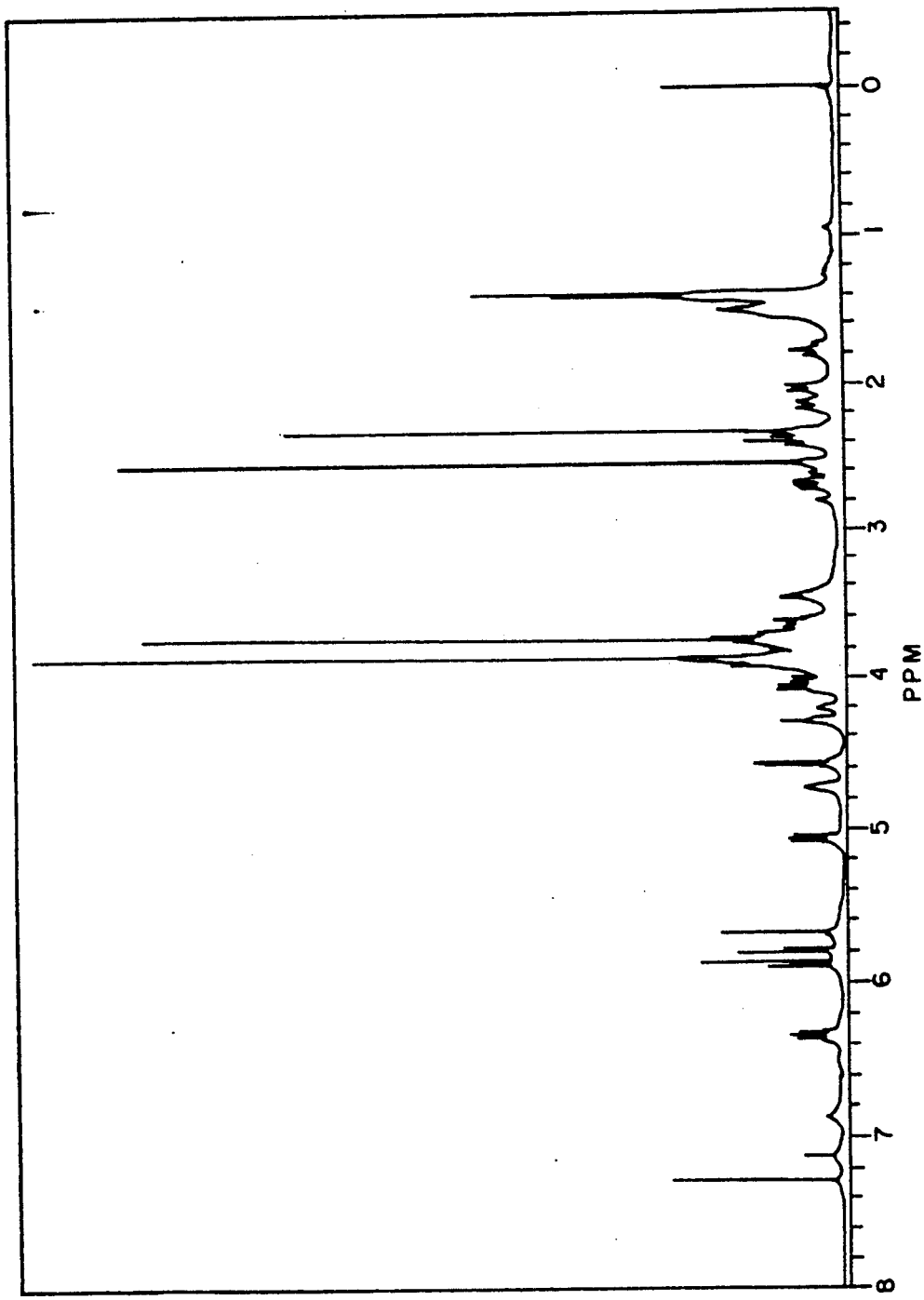
Figure 4:
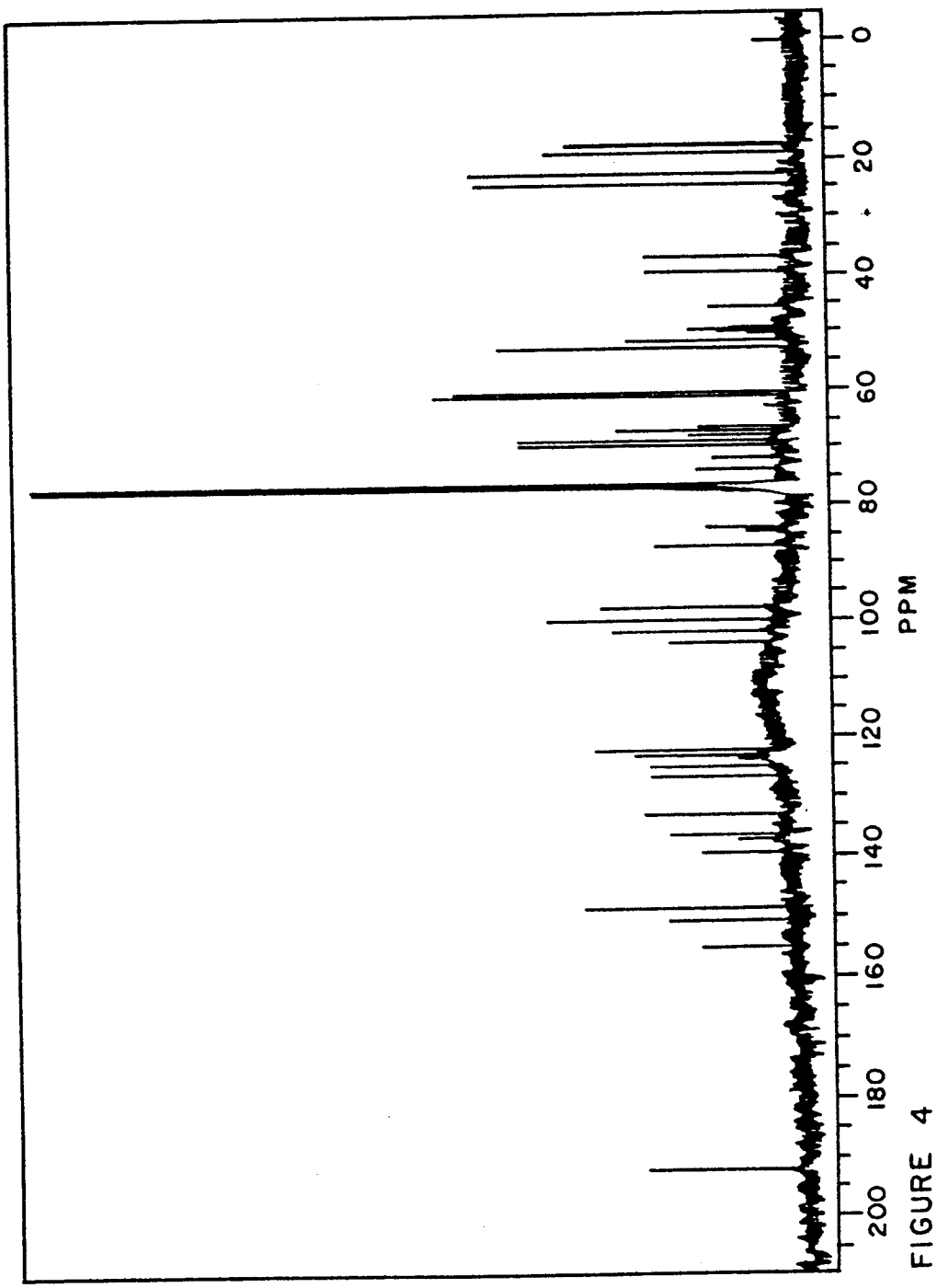
Figure 5:
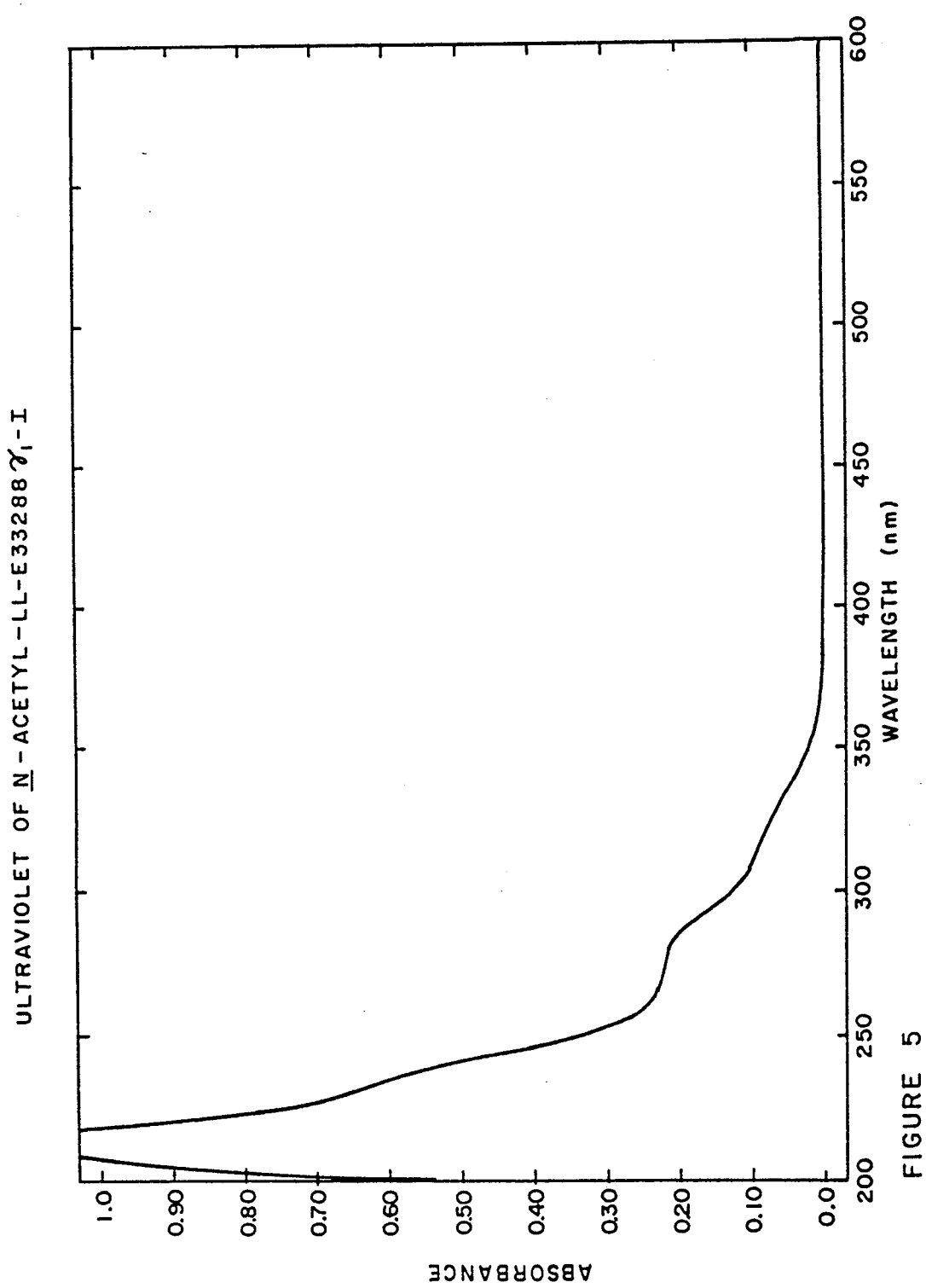
Figure 6:
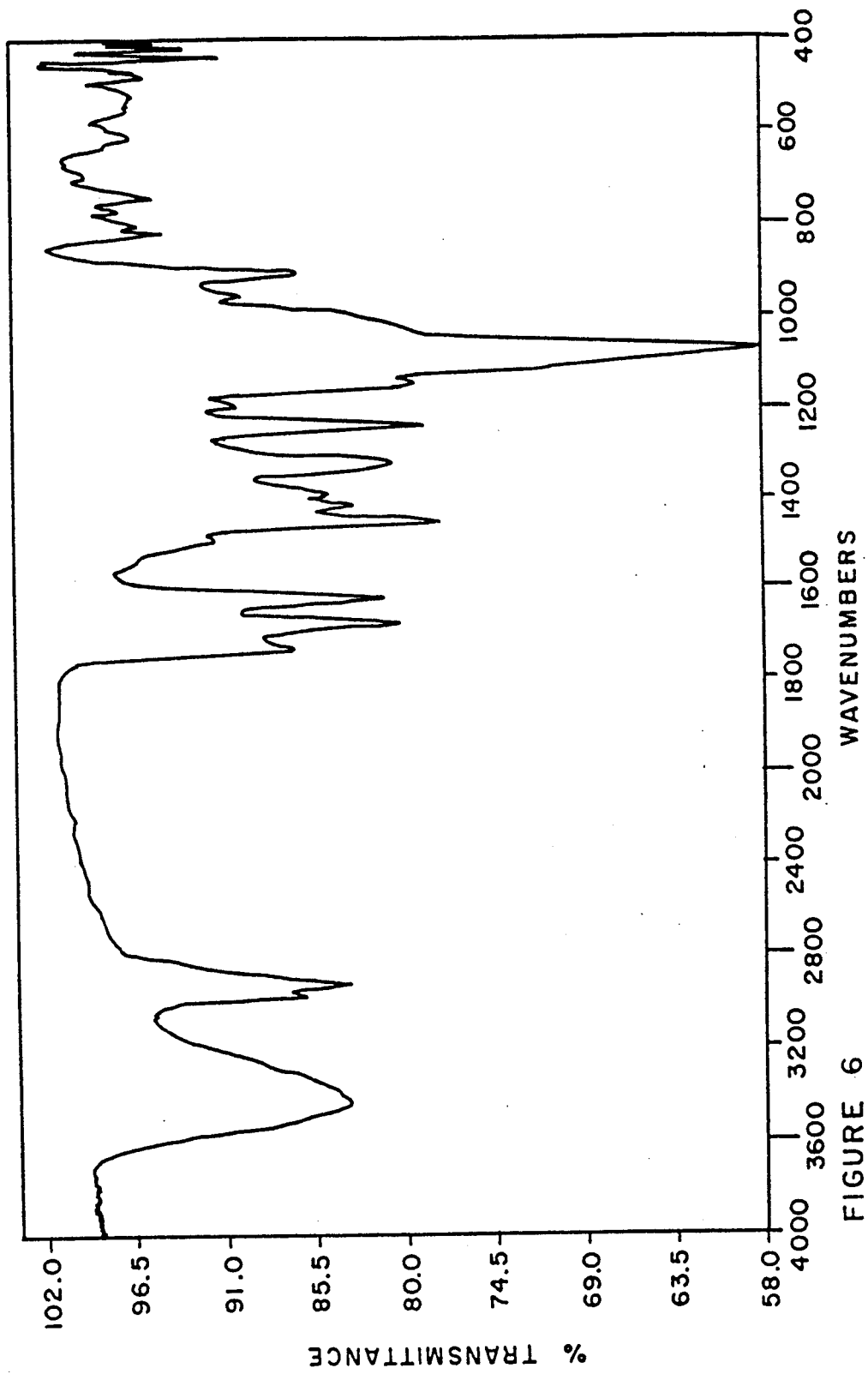
Figure 7:
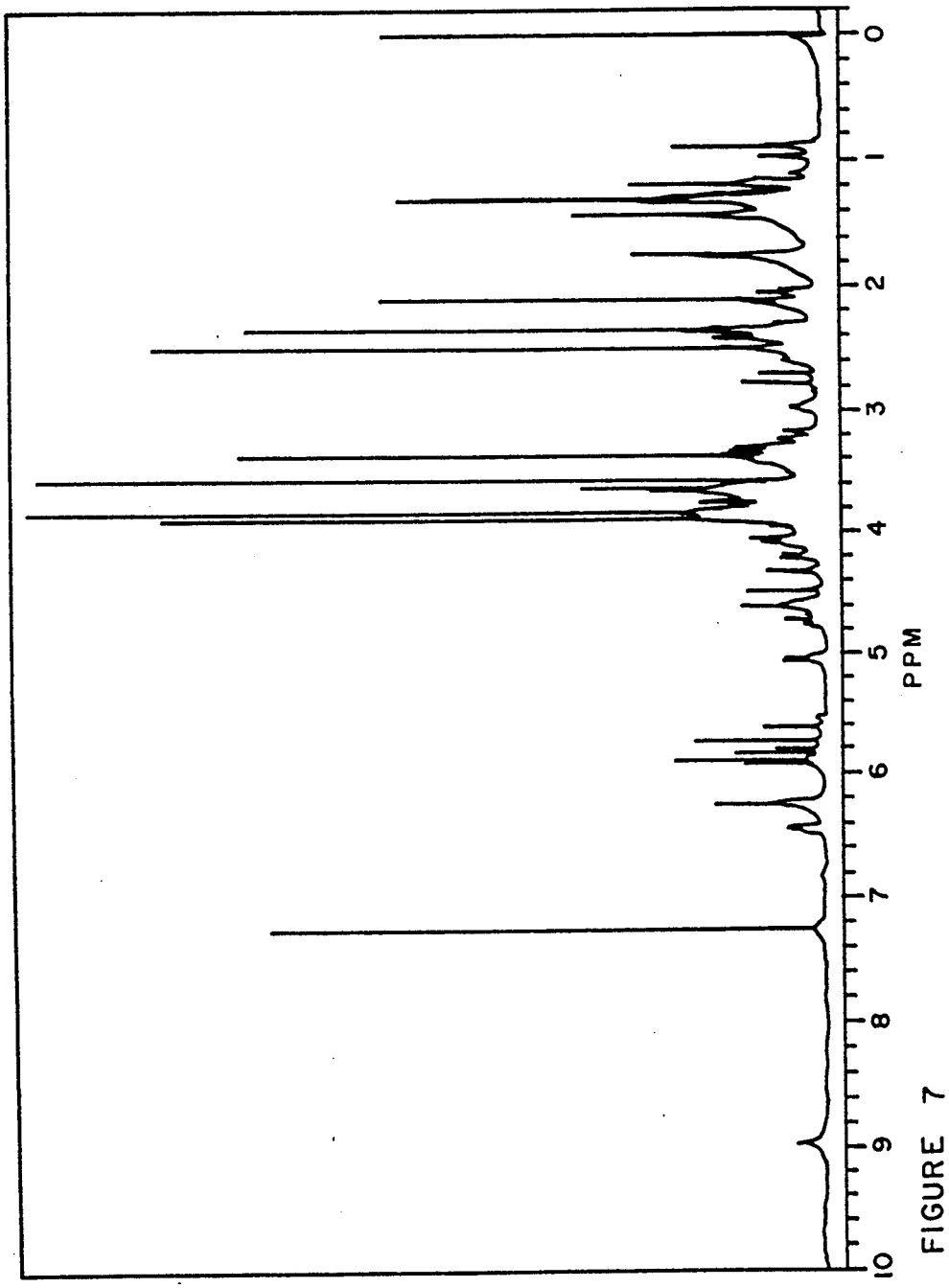
Figure 8:
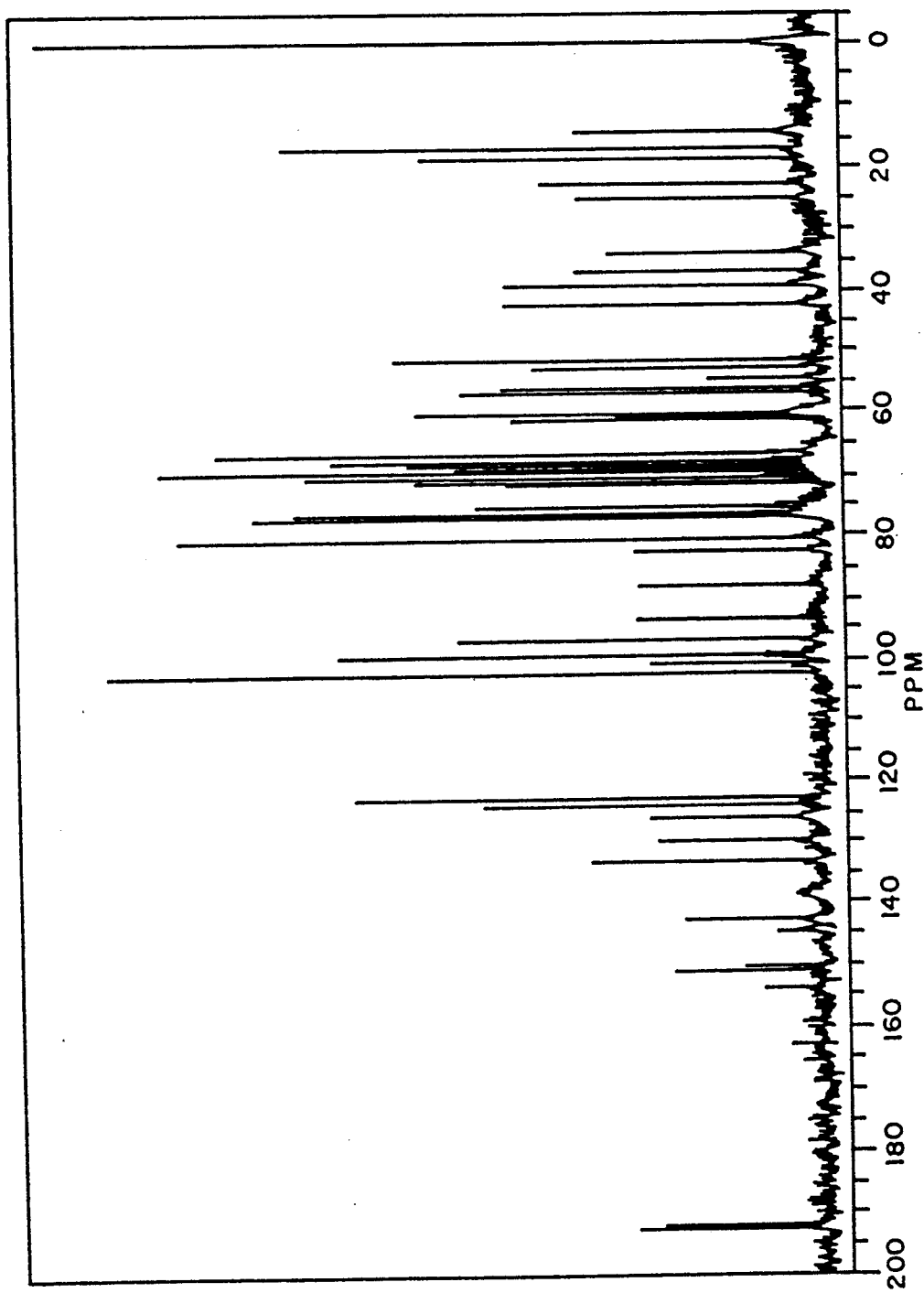

United States Patent [19]

Lee

[11] Patent Number: 5,037,651
[45] Date of Patent: Aug. 6, 1991

[54] DIHYDRO DERIVATIVES OF LL-E33288 ANTIBIOTICS

[75] Inventor: May D. Lee, Monsey, N.Y.

[73] Assignee: American Cyanamid Company, Stamford, Conn.

[21] Appl. No.: 4,154

[22] Filed: Jan. 30, 1987

[51] Int. Cl.$^5$ .................... A61K 35/74; A61K 31/70; A61K 37/02; C12P 1/06

[52] U.S. Cl. ........................................ 536/4.1; 514/18; 514/25; 514/53; 536/16.8; 536/17.2; 536/17.3; 536/17.4; 536/17.5; 536/17.6; 536/18.1; 530/322; 435/74; 435/169; 435/867; 424/117

[58] Field of Search .................... 536/16.8, 17.6, 18.1, 536/17.5; 424/117; 514/18, 25, 53

[56] References Cited

U.S. PATENT DOCUMENTS

| | | | |
|---|---|---|---|
| 4,530,835 | 7/1985 | Bunge et al. | 424/117 |
| 4,539,203 | 9/1985 | Brankiewicz et al. | 424/117 |
| 4,552,867 | 11/1985 | Martin et al. | 536/16.8 |
| 4,554,162 | 11/1985 | Young et al. | 424/117 |
| 4,675,187 | 6/1987 | Konishi et al. | 424/117 |

OTHER PUBLICATIONS

Bunge et al., Chemical Abstracts, vol. 102, 1985, No. 109431s.
Kiyoto et al., Chemical Abstracts, vol. 103, 1985, No. 101591u.

Primary Examiner—Johnnie R. Brown
Assistant Examiner—Elli Peselev

[57] ABSTRACT

Dihydro derivatives of LL-E33288, BBM-1075 FR-900405, FR-900406, PD 114759, PD 115028, CL-1577A, CL-1577B, CL-1577D, CL-1577E and CL-1724 antibiotics/antitumor agents are disclosed and described, including the degradation product of LL-E33288 antibiotics/antitumor agents dihydro-LL-E33288-pseudoaglycone.

26 Claims, 8 Drawing Sheets

DIHYDRO DERIVATIVES OF LL-E33288 ANTIBIOTICS

BACKGROUND OF THE INVENTION

The LL-E332B8 complex of antibiotics, having antibacterial and antitumor activity, are described and individually claimed in U.S. patent application, Ser. No. 009,321 now allowed, filed concurrently herewith, which application is a continuation-in-part of U.S. patent application Ser. No. 787,066, filed Oct. 17, 1985 now abandoned, which application is a continuation-in-part of U.S. patent application, Ser. No. 672,031, filed Nov. 16, 1984 now abandoned.

The application, Ser. No. 787,066, filed Oct. 17, 1985, defines the individual components, namely LL-E33288$\alpha_1$-Br, LL-E33288$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-33288$\beta_1$-Br, LL-E33288$\beta_1$-I, LL-E33288$\beta_2$-Br, LL-E33288$\beta_2$-I, LL-E33288$\gamma_1$-Br, LL-E33288$\gamma_1$-I, and LL-E33288$\delta_1$-I by specific physical and chemical characteristics, as well as detailing procedures for obtaining these components from the aerobic fermentation of a new *Micromonospora echinospora* spp *calichensis*, NRRL-15839, and a derived mutant NRRL-15975.

All of the information contained in U.S. patent application, Ser. No. 009,321 now allowed, filed concurrently herewith is incorporated herein by reference.

In addition to the above, other antibiotics which are described in the literature are pertinent to this invention.

1) Esperamicin BBM-1675, a novel class of potent antitumor antibiotics. Physico-chemical data and partial structure, M. Konishi, et al., J. Antibiotics, 38, 1605 (1985); U. K. Patent application GB 2,141,425A, May 15, 1984.

2) New antitumor antibiotics, FR-900405 and FR-900406; Taxonomy of the producing strain, M. Iwami, et al., J. Antibiotics, 38, 835 (1985). New antitumor antibiotics FR-900405 and FR-900406, production, isolation, characterization and antitumor activity, S. Kiyoto, et al., J. Antibiotics, 38, 840 (1985).

3) PD 114759 and PD 115028, novel antitumor antibiotics with phenomenal potency. Isolation and characterization, R. H. Bunge, et al., J. Antibiotics, 37, 1566 (1984). Biological and biochemical activities of the novel antitumor antibiotic PD 114759 and related derivatives, D. W. Fry, et al., Investigational New Drugs, 4, 3 (1986).

4) New antibiotic complex CL-1577A and CL-1577B produced by Streptomyces sp ATCC 39363. European Patent application 0,132,082,A2.

5) CL-1577D and CL-1577E Antibiotic antitumor compounds, their production and use. U.S. Pat. No. 4,539,203.

6) CL-1724 Antibiotic compounds, their production and use. U.S. Pat. No. 4,554,162.

All of the information regarding these antibiotics in the above cited references is incorporated herein by reference.

DESCRIPTION OF THE INVENTION

This invention is concerned with the dihydro derivatives of the LL-E33288 antibiotics, with the dihydro-LL-E33288-pseudoaglycone which is a degradation product of the LL-E33288 antibiotics and with the dihydro derivatives of antibiotics BBM-1675, FR-900405, FR-900406, PD 114759, PD 115028, CL-1577A, CL-1577B, CL-1577D, CL-1577E and CL-1724 referred to above.

The dihydro derivatives of the LL-E33288 antibiotics have the following proposed structures:

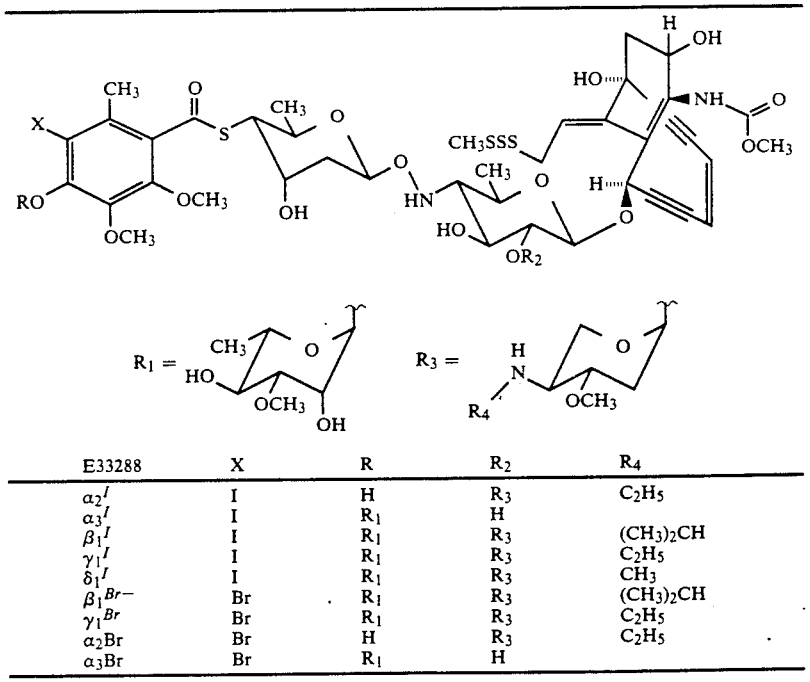

| E33288 | X | R | $R_2$ | $R_4$ |
|---|---|---|---|---|
| $\alpha_2^I$ | I | H | $R_3$ | $C_2H_5$ |
| $\alpha_3^I$ | I | $R_1$ | H | |
| $\beta_1^I$ | I | $R_1$ | $R_3$ | $(CH_3)_2CH$ |
| $\gamma_1^I$ | I | $R_1$ | $R_3$ | $C_2H_5$ |
| $\delta_1^I$ | I | $R_1$ | $R_3$ | $CH_3$ |
| $\beta_1^{Br-}$ | Br | $R_1$ | $R_3$ | $(CH_3)_2CH$ |
| $\gamma_1^{Br}$ | Br | $R_1$ | $R_3$ | $C_2H_5$ |
| $\alpha_2$Br | Br | H | $R_3$ | $C_2H_5$ |
| $\alpha_3$Br | Br | $R_1$ | H | |

The dihydro-LL-E33288-pseudoaglycone is derived from the LL-E33288-pseudoaglycone by treating the LL-E33288-pseudoaglycone with sodium borohydride in the solvent ethanol and in the presence of methyl iodide.

The dihydro-LL-E33288-pseudoaglycone has the following proposed structure:

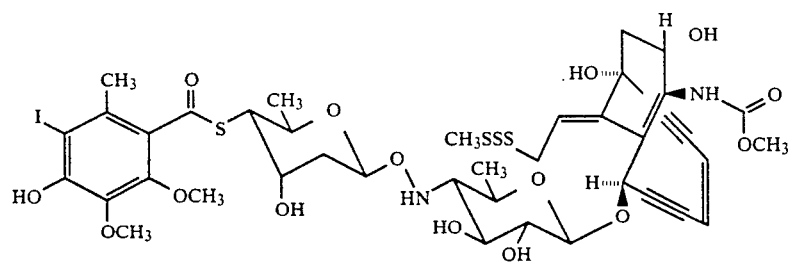

and the following physico-chemical characteristics:

a) ultraviolet absorption spectrum: as shown in FIG. I (methanol);

b) infrared absorption spectrum: as shown in FIG. II (KBr disc);

c) proton magnetic resonance spectrum: as shown in FIG. III (300MHz, CDCl$_3$); and d) carbon-13 magnetic resonance spectrum: as shown in FIG. IV (75MHz, CDCl$_3$).

The dihydro derivatives of the LL-E33288 components, the LL-E33288-pseudoaglycone and antibiotics BBM-1675, FR-900405, FR-900406, PD 114759, PD 115028, CL-1577A, CL-1577B, CL-1577D, CL-1577E and CL-1724 may be prepared by adding an alkyl iodide such as methyl iodide to an ethanolic solution of the antibiotic, cooling the solution in an ice-water bath, adding portionwise an ethanolic solution of sodium borohydride, decomposing the borate complex in the completed reaction with an ethanolic solution of acetic acid, concentrating the reaction mixture, redissolving in ethyl acetate, reconcentrating to dryness, redissolving in ethyl acetate, filtering, concentration to a small volume, precipitation with hexane and purification by chromatography.

The dihydro derivatives described above and the N-acetyl derivatives to be described hereinafter are active as antibacterial agents when tested by the standard agar dilution method. This activity was determined against a spectrum of gram-positive and gram-negative bacteria. Mueller-Hinton agar containing two-fold decreasing concentrations of the compounds was poured into petri plates. The agar surface was inoculated with 1 to $5 \times 10^6$ colony-forming units of bacteria by means of the Steers replicating device. The lowest concentration of the compound that inhibited growth of a bacterial strain after about 18 hours of incubation at approximately 35° C. was recorded as the minimal inhibitory concentration (MIC) for that strain. The results appear in Table I.

TABLE I

| | | Minimal Inhibitory Concentration (mcg/ml) | |
|---|---|---|---|
| Organism | | Dihydro-LL-E33288gamma$_1$-I | N-Acetyl-LL-E33288gamma$_1$-I |
| Escherichia coli | CMC 84-11 | 2 | >2 |
| Escherichia coli | No. 311 (MP) | 2 | >2 |
| Escherichia coli | ATCC 25922 | 1 | >2 |
| Klebsiella pneumoniae | CMC 84-5 | >2 | >2 |
| Klebsiella pneumoniae | AD (MP) | 1 | 2 |
| Enterobacter cloacae | CMC 84-4 | 2 | >2 |
| Enterobacter aerogenes | IO 83-44 | 2 | >2 |
| Serratia marcescens | CMC 83-27 | 2 | >2 |
| Serratia marcescens | F-35 (MP) | 2 | >2 |
| Morganella morganii | IO 83-18 | 1 | >2 |
| Providencia stuartii | CMC 83-82 | 2 | >2 |
| Citrobacter diversus | K-82-24 | 2 | >2 |
| Citrobacter freundii | IO 83-18 | 2 | >2 |
| Acinetobacter sp | CMC 83-89 | 2 | >2 |
| Acinetobacter sp | IO 83-49 | >2 | >2 |
| Pseudomonas aeruginosa | 12-4-4 (MP) | 2 | >2 |
| Pseudomonas aeruginosa | ATCC 27853 | 2 | >2 |
| Staphylococcus aureus | Smith (MP) | 0.004 | 0.008 |
| Staphylococcus aureus | SSC 82-21 | 0.004 | 0.06 |
| Staphylococcus aureus | ATCC 25923 | 0.06 | 0.06 |
| Staphylococcus aureus | SSC 82-20 | 0.06 | 0.06 |
| Staphylococcus aureus | SSC 82-23 | 0.008 | 0.06 |
| Staphylococcus aureus | SSC 82-24 | 0.002 | 0.06 |
| Staphylococcus aureus | SSC 82-54 | 0.06 | 0.12 |
| Staphylococcus epidermidis | CMC 83-133 | 0.015 | 0.12 |
| Staphylococcus epidermidis | ATCC 12228 | 0.015 | 0.12 |
| Streptococcus faecalis | ATCC 29212 | 0.001 | 0.12 |
| Streptococcus faecalis | CMC 83-53 | 0.015 | 0.12 |
| Streptococcus faecalis | IO 83-28 | 0.015 | 0.12 |

The above described dihydro and N-acetyl derivatives were tested to determine their activity in the Biochemical Induction Assay (BIA), a bacterial assay system which specifically measures the ability of an agent to directly or indirectly initiate DNA damage. The indicator organism for this test is an E. colilambda lysogen, genetically constructed such that a DNA damaging event results in the expression of the gene for the enzyme β-galactosidase. This enzyme can be determined qualitatively or quantitatively by biochemical assay as an indication that DNA damage has occurred.

A modified version of the quantitative liquid BIA disclosed by Elespuru, R. and Yarmolinsky, M. Environmental Mutagenesis, 65 (1979) was employed to evaluate the dihydro and N-acetyl derivatives, which were active in the test.

In addition to the above, this invention is concerned with N-acetyl derivatives of the LL-E33288 antibiotics and with the N-acetyl derivatives of antibiotics BBM-1675, FR-900405, FR-900406, PD 114759, PD 115028, CL-1577A, CL-1577B, CL-1577D, CL-1577E and CL-1724 referred to above.

The proposed structure of one such compound, N-acetyl-LL-E33288$\gamma_1$I is shown below:

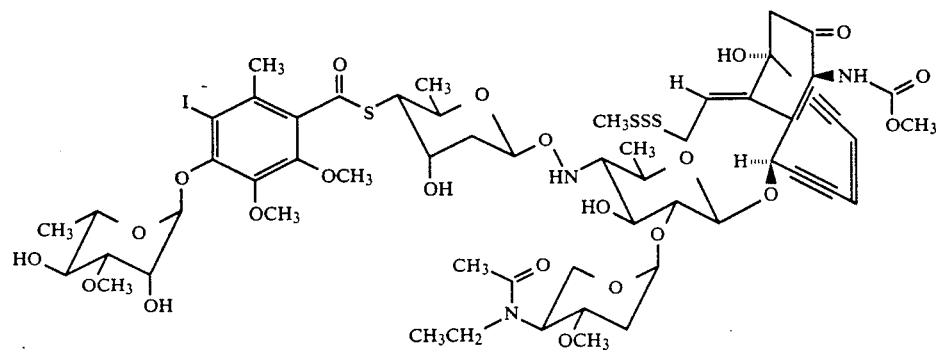

The physico-chemical characteristics of N-acetyl-LL-E33288$\gamma_1$-I are described below:

a) molecular weight: 1409, determined by FAB-MS;

b) molecular formula: $C_{57}H_{76}N_3O_{22}IS_4$, exact mass for M+H was determined by high resolution FAB-MS to be 410.2954 for $C_{57}H_{77}N_3O_{22}IS_4$;

c) ultraviolet absorption spectrum: as shown in FIG. V (methanol);

d) infrared absorption spectrum: as shown in FIG. VI (KBr disc);

e) proton magnetic resonance spectrum: as shown in FIG. VII (300MHz, $CDCl_3$);

f) Carbon-13 magnetic resonance spectrum: as shown in FIG. VIII (75.43MHz, $CDCl_3$, ppm from TMS) significant peaks as listed below:

| | | | | | |
|---|---|---|---|---|---|
| 14.0 q | 17.6 q | 17.7 q | 19.0 q | 22.4 q | 22.8 q |
| 25.4 q | 36.7 t | 36.9 t | 39.2 t | 47.6 t | 51.6 d |
| 52.4 q | 53.1 t | 57.0 q | 57.2 q | 58.8 t | 60.9 q |
| 61.7 q | 64.4 d | 67.0 d | 68.1 d | 68.4 d | 69.0 d |
| 69.1 d | 70.5 d | 71.1 d | 71.7 s | 71.9 d | 72.4 d |
| 77.6 d | 80.8 d | 83.2 s | 87.0 d | 93.5 s | 97.9 d |
| 98.1 s | 99.7 d | 100.9 s | 101.3 d | 102.6 d | 123.2 d |
| 124.5 d | 127.1 d | 130.2 s | 133.4 s | 136.5 s | 142.9 s |
| 143.0 s | 150.6 s | 151.5 s | 155.0 s | 172.3 s | 191.9 s |
| 192.1 s. | | | | | |

In addition to being active antibacterial agents, the N-acetyl derivatives are active in the BIA, and are also active as antitumor agents in the familiar P388, L1210, B-16 and Colon 26 tests which are predictive of activity against these tumors in other warm-blooded animals.

These N-acetyl derivatives may be prepared by treating a methanolic solution of the parent antibiotic with acetic anhydride initially in an ice bath, then at ambient temperature.

The invention is further described by the following examples.

EXAMPLE 1

Preparation of Dihydro-LL-E33288$\gamma_1$-I

A 10 ml portion of methyl iodide was added to a solution of 126 mg of LL-E33288$\gamma_1$-I in 25 ml of ethanol and the mixture was cooled in an ice-water bath. To this was added 12 ml of a 0.1M ethanolic solution of sodium borohydride, in 2 ml portions. When the reaction was complete, the borate complex was decomposed by the addition of 1.2 ml of a 4M ethanolic solution of acetic acid. The reaction mixture was then concentrated to a golden yellow residue which was redissolved in ethyl acetate and then reconcentrated to dryness. This residue was redissolved in ethyl acetate, the insolubles filtered off, the filtrate concentrated to a small volume and precipitated by the addition of hexane. The 301 mg of crude dihydro-LL-E33288$\gamma_1$-I was purified by chromatography on a Bio-Sil A (20-44$\mu$) column, eluting with dichloromethane:methanol (92:8), giving 57 mg of pure dihydro-LL-E33288$\gamma_1$-I as a 30:0 mixture of two regio isomers.

EXAMPLE 2

Preparation of Dihydro-LL-E33288-pseudoaglycone

A 10 ml portion of methyl iodide was added to a solution of 112 mg of LL-E33288-pseudoaglycone in 25 ml of ethanol and this mixture was cooled in an ice-water bath. To this was added 12 ml of a 0.025M ethanolic sodium borohydride in 2 ml portions. When the reaction was complete, the borate complex was decomposed by the addition of 1.2 ml of a 1M ethanolic solution of acetic acid. The reaction mixture was then concentrated to a golden yellow residue, redissolved in ethyl acetate and then reconcentrated to dryness. This residue was redissolved in ethyl acetate, the insolubles filtered off, the filtrate concentrated to a small volume and precipitated by the addition of hexane. The 128 mg of crude dihydro-LL-E33288-pseudoaglycone was purified by chromatography on a Bio-Sil A (20-44$\mu$) column, eluting with dichloromethane:methanol (97:3), giving 42 mg of pure dihydro-LL-E33288-pseudoaglycone.

EXAMPLE 3

Preparation of N-acetyl-LL-E33288$\gamma_1$-I

Acetic anhydride (3 ml) was added dropwise to a methanolic solution of partially purified LL-E33288$\gamma_1$-I (421 mg, 32% pure, in 100 ml) cooled in an ice-water bath. The reaction mixture was allowed to stir at 0° C. for 1.5 hours then warmed slowly to room temperature and the reaction was allowed to continue for another 2.5 hours. It was then concentrated in vacuo, the residue was redissolved in ethyl acetate and precipitated by addition of diethyl ether and hexane. The precipitated crude N-acetyl-LL-E33288$\gamma_1$-I was purified by chromatography on a Bio-Sil A (23-40$\mu$) column eluting with ethyl acetate:methanol (96:4) to give 107 mg of analytically pure N-acetyl-LL-E33288γ₁-I.
What is claimed is:
1. A compound dihydro-LL-E33288α₂-Br of the formula:
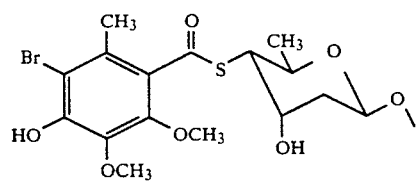
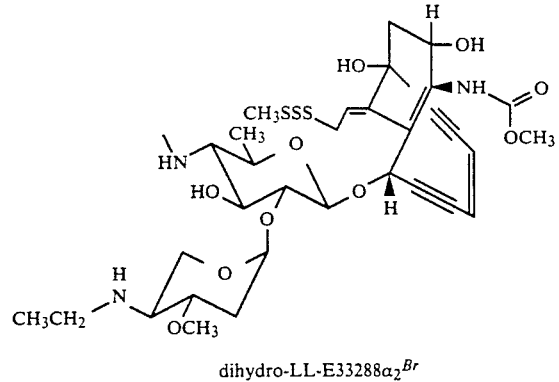
dihydro-LL-E33288α₂$^{Br}$
2. A compound dihydro-LL-E33288α₂-I of the formula:
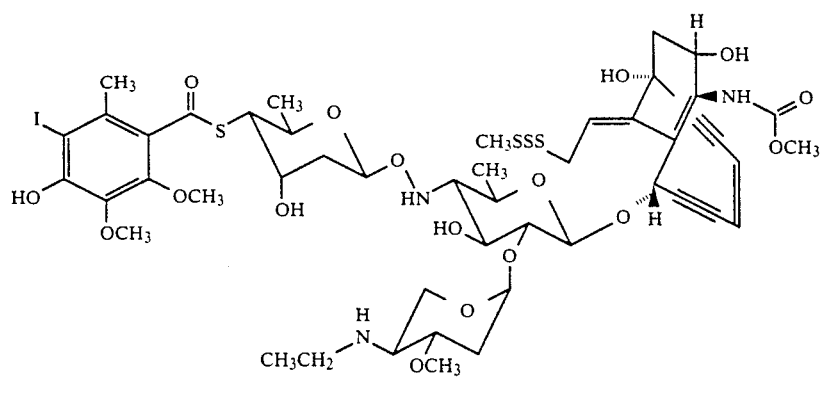
dihydro-LL-E33288α₂$^{I}$
3. A compound dihydro-LL-E33288α₃-Br of the formula:
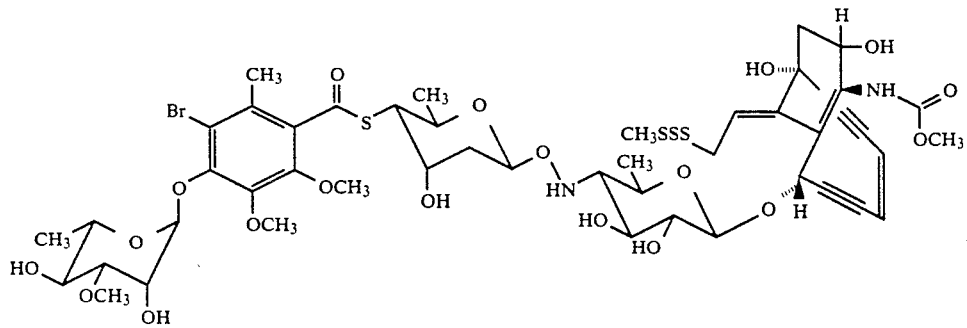
dihydro-LL-E33288α₃$^{Br}$
4. A compound dihydro-LL-E33288α₃-I of the formula:

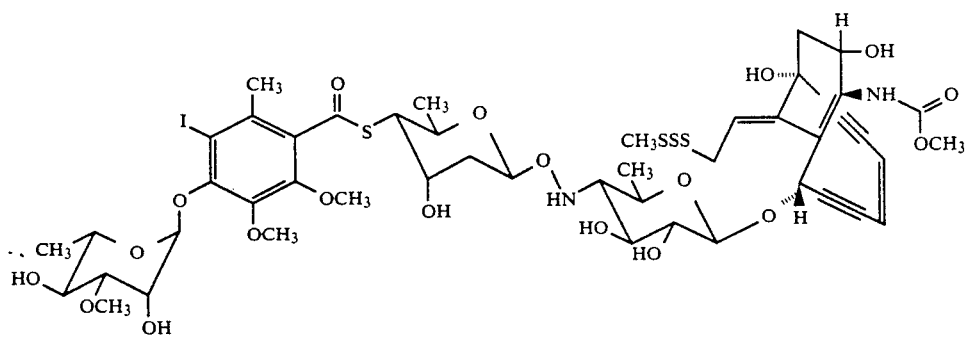

dihydro-LL-E33288α₃ⁱ

5. A compound dihydro-LL-E33288β₁-Br of the formula:

8. A compound dihydro-LL-E33288β₂-I prepared by reducing LL-E33288β₂-I with sodium borohydride in

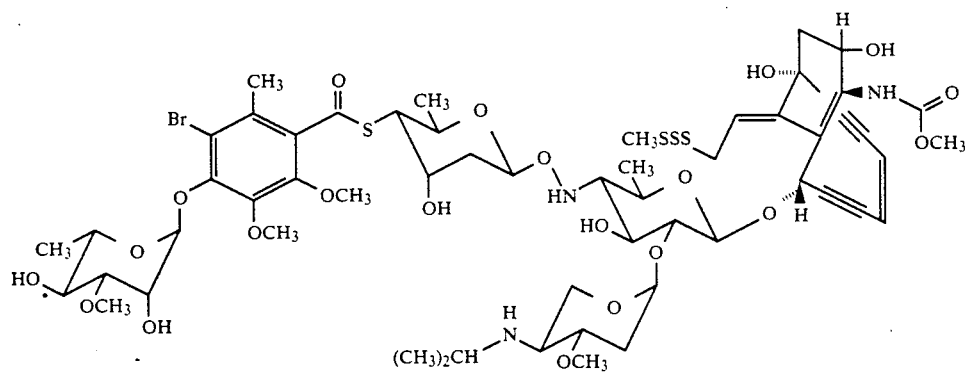

dihydro-LL-E33288β₁^Br

6. A compound dihydro-LL-E33288β₁-I of the formula:

the presence of an alkyl iodide.

9. A compound dihydro-LL-E33288γ₁-Br of the for-

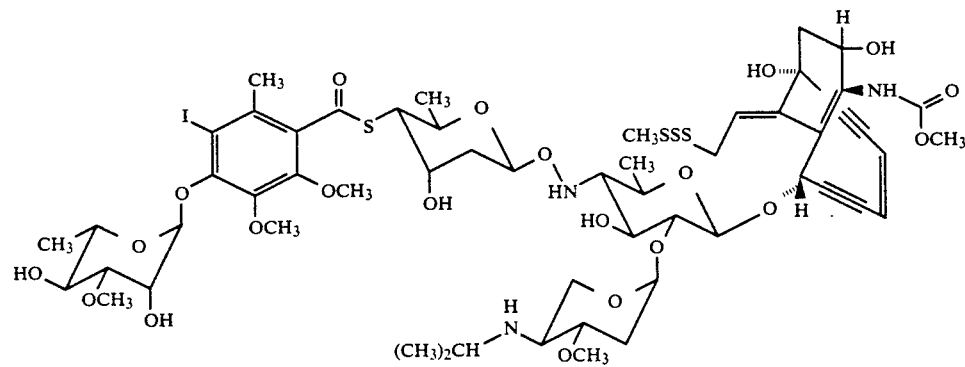

dihydro-LL-E33288β₁ⁱ

7. A compound dihydro-LL-E33288β₂-Br prepared by reducing LL-E33288β₂-Br with sodium borohydride in the presence of an alkyl iodide.

mula:

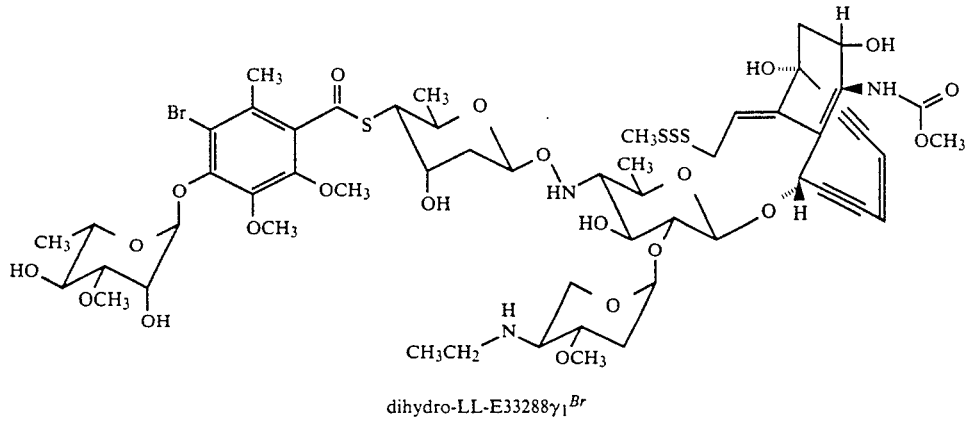

dihydro-LL-E33288γ₁$^{Br}$

10. A compound dihydro-LL-E33288γ₁-I of the formula:

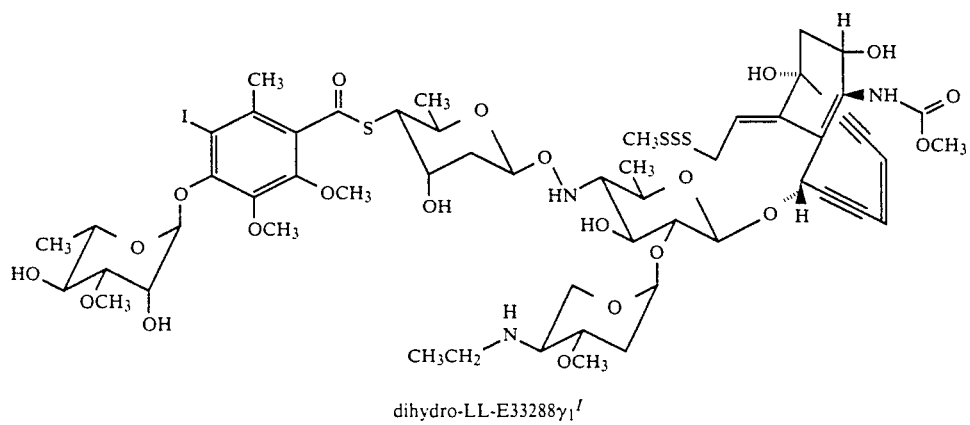

dihydro-LL-E33288γ₁$^{I}$

11. A compound dihydro-LL-E33288δ₁-I of the formula:

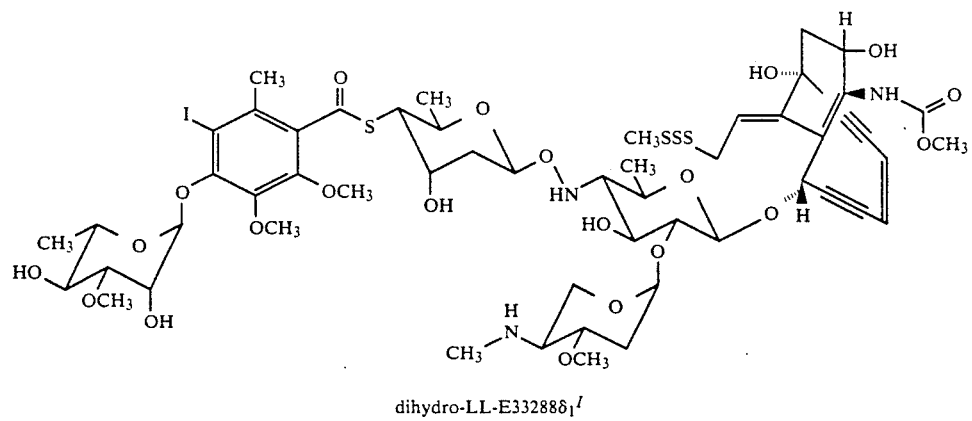

dihydro-LL-E33288δ₁$^{I}$

12. A compound dihydro-BBM-1675 prepared by reducing BBM-1675 with sodium borohydride in the presence of an alkyl iodide.

13. A compound dihydro-FR-900405 prepared by reducing FR-900405 with sodium borohydride in the presence of an alkyl iodide.

14. A compound dihydro-FR-900406 prepared by reducing FR-900406 with sodium borohydride in the presence of an alkyl iodide.

15. A compound dihydro-PD-114759 prepared by reducing PD-114759 with sodium borohydride in the presence of an alkyl iodide.

16. A compound dihydro-PD-115028 prepared by reducing PD-115028 with sodium borohydride in the presence of an alkyl iodide.

17. A compound dihydro-CL-1577A. prepared by reducing CL-1577A with sodium borohydride in the presence of an alkyl iodide.

18. A compound dihydro-CL-1577B prepared by reducing CL-1577B with sodium borohydride in the presence of an alkyl iodide.

19. A compound dihydro-CL-1577D prepared by reducing CL-1577D with sodium borohydride in the presence of an alkyl iodide.

20. A compound dihydro-CL-1577E prepared by reducing CL-1577E with sodium borohydride in the presence of an alkyl iodide.

21. A compound dihydro-CL-1724 prepared by reducing CL-1724 with sodium borohydride in the presence of an alkyl iodide.

22. A compound dihydro-LL-E33288-pseudoaglycone, prepared by treating a dilute methanolic solution of LL-E33288$\gamma_1$-I with an ion exchange resin, giving LL-E33288-pseudoaglycone which is then reacted with an alkyl iodide in ethanol cooled to ice bath temperature, followed by reaction with ethanolic sodium borohydride, decomposition with acetic acid, precipitation from ethyl acetate solution with hexane and purification by chromatography, giving the dihydro-LL-E33288-pseudoaglycone having the following characteristics:
   a) an ultraviolet absorption spectrum: as shown in FIG. I (methanol);
   b) an infrared absorption spectrum: as shown in FIG. II (KBr disc);
   c) a proton magnetic resonance spectrum: as shown in FIG. III (300MHz, CDCl$_3$); and
   d) a carbon-13 magnetic resonance spectrum: as shown in FIG. IV (75MHz, CDCl$_3$) of the formula:

23. A method for treating bacterial infections in warm-blooded animals which comprises administering to said animals an antibacterially effective amount of a compound selected from any one of claims 1-22.

24. A method for treating tumors in warm-blooded animals which comprises administering to said animals an oncolytic amount of a compound selected from any one of claims 1-22.

25. A composition of matter in dosage unit form, comprising an antibacterially effective amount of a compound selected from any one of claims 1-22 in association with a pharmaceutically acceptable carrier.

26. A process for producing the compounds of any one of claims 1-22 which comprises adding an alkyl iodide to an ethanolic solution of the antibiotic selected from the group consisting of LL-E33288$\alpha_2^{Br}$, LL-E33288$\alpha_2^I$, LL-E33288$\alpha_3^{Br}$, LL-E33288$\alpha_3^I$, LL-E33288$\beta_1^{Br}$, LL-E33288$\beta_1^I$, LL-E33288$\beta_2^{Br}$, LL-E33288$\beta_2^I$, LL-E33288$\gamma_1^{Br}$, LL-E33288$\gamma_1^I$, LL-E33288$\delta^I$, BBM-1675, FR-900405, FR-900406, PD-114759, PD-115028, CL-1577A, CL-1577B, CL-1577D, CL-1577E, CL-1524 or LL-E33288 pseudoaglycone, cooling the solution to ice-bath temperature, adding an ethanolic solution of sodium borohydride, decomposing the borate complex by the addition of acetic acid, precipitation from an ethyl acetate solution by the addition of hexane and purification by chromatography.

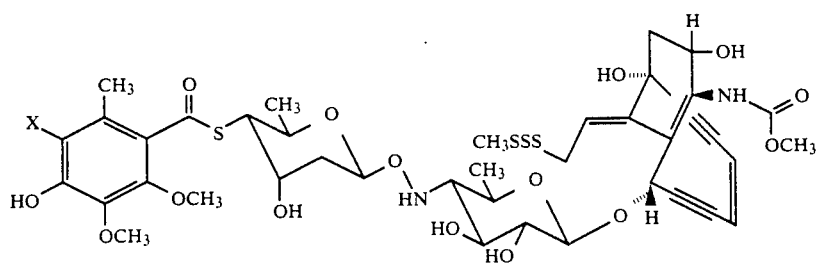

X = Br or I dihydro-LL-E33288 pseudoaglycone

* * * * *